(12) United States Patent
Aulombard et al.

(10) Patent No.: US 7,202,267 B2
(45) Date of Patent: Apr. 10, 2007

(54) ACYLOXYPYRROLIDINE DERIVATIVES, PREPARATION THEREOF AND APPLICATION THEREOF IN THERAPEUTIC

(75) Inventors: Alain Aulombard, Montpellier (FR); Georges Garcia, Frontignan (FR); Antoine Pradines, Roquettes (FR); Claudine Serradeil-Le Gal, Escalquens (FR); Jean Wagnon, Montpellier (FR)

(73) Assignee: Sanofi-aventis, Paris (FR)

( * ) Notice: Subject to any disclaimer, the term of this patent is extended or adjusted under 35 U.S.C. 154(b) by 23 days.

(21) Appl. No.: 11/038,384

(22) Filed: Jan. 19, 2005

(65) Prior Publication Data

US 2005/0192335 A1    Sep. 1, 2005

Related U.S. Application Data

(63) Continuation of application No. PCT/FR03/02262, filed on Jul. 17, 2003.

(30) Foreign Application Priority Data

Jul. 19, 2002    (FR) .................................. 02 09242

(51) Int. Cl.
*A61K 31/404*    (2006.01)
*C07D 403/04*    (2006.01)
(52) U.S. Cl. ...................... 514/414; 548/466
(58) Field of Classification Search ............... 548/466; 514/414
See application file for complete search history.

(56) References Cited

FOREIGN PATENT DOCUMENTS

WO    WO 01/55130    8/2001

OTHER PUBLICATIONS

Cancer and Metastasis Reviews (1998), 17(1), 91-106.*
Science (1999), vol. 286, 531-537.*
Akerlund, Prog. Brain Res. vo. 139, p. 359-65 (2002) (abstract).*
Paranjape et al. Expert Opinion on Investigational Drugs, vol. 10(5), p825-834 (2001).*

* cited by examiner

*Primary Examiner*—Rebecca Anderson
(74) *Attorney, Agent, or Firm*—Balaram Gupta

(57) ABSTRACT

The invention relates to acyloxypyrrolidine derivatives of general formula (I):

in which:
$R_1$ represents a hydrogen atom, a $(C_1-C_6)$alkyl, a $(C_3-C_6)$ cycloalkyl, a group —$CH_2CH_2COOH$ or a group —$NR_2R_3$; $R_2$ and $R_3$ each represent, independently, a hydrogen atom or a $(C_1-C_6)$alkyl. Also disclosed and claimed are the method of preparation of the compounds of the invention and their application in therapeutics.

16 Claims, No Drawings

ACYLOXYPYRROLIDINE DERIVATIVES, PREPARATION THEREOF AND APPLICATION THEREOF IN THERAPEUTIC

This application is a continuation of International application No. PCT/FR2003/002,262, filed Jul. 17, 2003; which claims the benefit of priority of French Patent Application No. 02/09,242, filed Jul. 19, 2002, both of which are incorporated herein by reference in their entirety.

BACKGROUND OF THE INVENTION

1. Field of the Invention

The present invention relates to acyloxypyrrolidine derivatives, to the preparation thereof and to the application thereof in therapeutics.

The compounds according to the present invention exhibit an affinity and selectivity for $V_{1b}$ receptors, or for both $V_{1b}$ and $V_{1a}$ receptors, for arginine-vasopressin (AVP).

2. Description of the Art

AVP is a hormone known for its antidiuretic effect and its effect in the regulation of arterial pressure. It stimulates several types of receptor: $V_1$ ($V_{1a}$, $V_{1b}$) and $V_2$. These receptors are located in particular in the liver, the vessels (coronary, renal, cerebral), the platelets, the kidney, the uterus, the adrenal glands, the pancreas, the central nervous system and the pituitary gland. AVP thus exerts cardiovascular, hepatic, pancreatic, antidiuretic and platelet-aggregating effects and effects on the central and peripheral nervous system and on the uterine sphere.

The location of the various receptors is described in: S. JARD et al., Vasopressin and oxytocin receptors: an overview, in Progress in Endocrinology. H. IMURA and K. SHIZURNE ed., Experta Medica, Amsterdam, 1988, 1183–1188, and also in the following articles: J. Lab. Clin. Med., 1989, 114 (6), 617–632 and Pharmacol. Rev., 1991, 43 (1), 73–108.

More particularly, $V_{1a}$ receptors for AVP are located in many peripheral organs and in the brain. They have been cloned, in particular in rats and humans, and they regulate most of the known effects of AVP: platelet aggregation; uterine contractions; vessel contractions; secretion of aldosterone, of cortisol, of CRF (for corticotropin-releasing factor) and of adrenocorticotrophic hormone (ACTH); hepatic glycogenolysis, cell proliferation and the main central effects of AVP (hypothermia, memory, etc.).

$V_{1b}$ receptors were initially identified in the adenohypophysis of various animal species (rats, pigs, bovines, sheep, etc), including in humans (S. JARD et al., Mol. Pharmacol., 1986, 30, 171–177; Y. ARSENIJEVIC et al., J. Endocrinol., 1994, 141, 383–391; J. SCHWARTZ et al., Endocrinology, 1991, 129 (2), 1107–1109; Y. DE KEYSER et al., FEBS Letters, 1994, 356, 215–220), where they stimulate the release of adrenocorticotrophic hormone by AVP and potentiate the effects of CRF on the release of ACTH (G. E. GILLIES et al., Nature, 1982, 299, 355). In the hypothalamus, $V_{1b}$ receptors also induce direct release of CRF (Neuroendocrinology, 1994, 60, 503–508) and are, in these various respects, involved in situations of stress.

These $V_{1b}$ receptors have been cloned in rats, humans and mice (Y. DE KEYSER, FEBS, Letters, 1994, 356, 215–220; T. SUGIMOTO et al., J. Biol. Chem., 1994, 269 (43), 27088–27092; M. SAITO et al., Biochem. Biophys. Res. Commun., 1995, 212 (3), 751–757; S. J. LOLAIT et al., Neurobiology, 1996, 92, 6783–6787; M. A. VENTURA et al., Journal of Molecular Endocrinology, 1999, 22, 251–260) and various studies (in situ hybridization, PCR (polymerase chain reaction), etc.) reveal an ubiquitous location for these receptors in various central tissues, (brain, hypothalamus and adenohypophysis, in particular) and peripheral tissues (kidney, pancreas, adrenals, heart, lungs, intestine, stomach, liver, mesentery, bladder, thymus, spleen, uterus, retina, thyroid, etc.) and in some tumors (hypophyseal, pulmonary, etc.), suggesting a widespread biological and/or pathological role to these receptors and a potential involvement in various diseases.

By way of examples, in rats, studies have shown that AVP, via $V_{1b}$ receptors, regulates the endocrine pancreas by stimulating secretion of insulin and of glucagon (B. LEE et al., Am. J. Physiol. 269 (Endocrinal. Metab. 32): E1095–E1100, 1995) or the production of catecholamines in the adrenal medulla, which is the site of local synthesis of AVP (E. GRAZZINI et al., Endocrinology, 1996, 137 (a), 3906–3914). Thus, in the latter tissue, AVP, via these receptors, would have an essential role in certain types of adrenal pheochromocytomas which secrete AVP and, as a result, induce a large production of catecholamines, causing hypertension resistant to angiotensin II receptor antagonists and to angiotensin-converting enzyme inhibitors. The adrenal cortex is also rich in $V_{1a}$ receptors involved in the production of glucocorticoids and mineralocorticoids (aldosterone and cortisol). Via these receptors, AVP (circulating or locally synthesized) can induce aldosterone production with an efficiency comparable to that of angiotensin II (G. GUILLON et al., Endocrinology, 1995, 136 (3), 1285–1295). Cortisol is a powerful regulator of the production of ACTH, the stress hormone.

Recent studies have also shown that the adrenal glands are capable of directly releasing CRF and/or ACTH via activation of the $V_{1b}$ and/or $V_{1a}$ receptors carried by the cells of the medulla (G. MAZZOCCHI et al., Peptides, 1997, 18 (2), 191–195; E. GRAZZINI et al., J. Clin. Endocrinal. Metab., 1999, 84 (6), 2195–2203).

$V_{1b}$ receptors are also considered to be tumor markers. For example, ACTH-secreting tumors, namely certain pituitary tumors, and certain bronchial carcinomas (small cell lung cancers, SCLC), pancreatic carcinomas, adrenal carcinomas and thyroid carcinomas, inducing Cushing's syndrome in some cases (J. BERTHERAT et al., Eur. J. Endocrinol., 1996, 135, 173; G. A. WITTERT et al., Lancet, 1990, 335, 991–994; G. DICKSTEIN et al., J. Clin. Endocrinol. Metab., 1996, 81 (8), 2934–2941), overexpress $V_{1b}$ receptors. As regards $V_{1a}$ receptors, they are more specific markers for small cell lung cancers (SCLC) (P. J. WOLL et al., Biochem. Biophys. Res. Commun., 1989, 164 (1), 66–73). Thus, the compounds according to the present invention are obvious diagnostic tools and offer a novel therapeutic approach in the proliferation and detection of these tumors, even at an early stage (radiolabelling; SPECT, for Single Photon Emission Computed Tomography; PET Scan, for Positron Emission Tomography Scanner).

The abundant presence of the $V_{1b}$ receptor messenger in the stomach and intestines suggests that AVP is involved, via this receptor, in the release of gastrointestinal hormones such as cholecystokinin, gastrin or secretin (T. SUGIMOTO et al., Molecular cloning and functional expression of $V_{1b}$ receptor gene, in Neurohypophysis: Recent Progress of Vasopressin and Oxytocin Research; T. SAITO, K. KUROKAWA and S. YOSHIDA ed., Elsevier Science, 1995, 409–413).

International patent application WO 01/55130 describes a family of compounds which exhibit an affinity and a selectivity for $V_{1b}$ receptors, or for both $V_{1b}$ and $V_{1a}$ receptors, for arginine-vasopressin.

More particularly, a selective antagonist for V$_{1b}$ receptors, (2S,4R)-1-[5-chloro-1-[(2,4-dimethoxyphenyl)sulfonyl]-3-(2-methoxyphenyl)-2-oxo-2,3-dihydro-1H-indol-3-yl]-4-hydroxy-N,N-dimethyl-2-pyrrolidinecarboxamide, the levorotatory isomer (hereinafter referred to as compound A), has been described (WO 01/55130; J. Pharmacol. Exp. Ther., 2002, 300 (3), 1122–1130).

All of the references described herein are incorporated herein by reference in their entirety.

SUMMARY OF THE INVENTION

Novel compounds, acyloxypyrrolidine derivatives, have now been found which exhibit an affinity and a selectivity for V$_{1b}$ receptors, or for both V$_{1b}$ and V$_{1a}$ receptors, for arginine-vasopressin.

A subject of the present invention is compounds corresponding to formula (I):

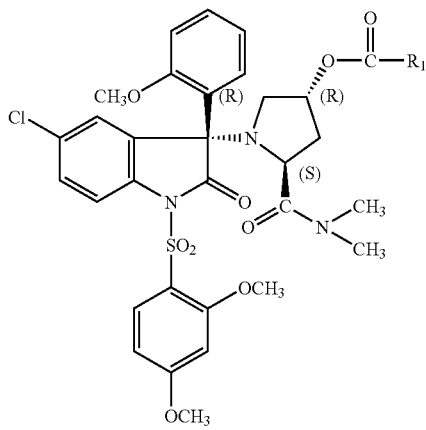

in which:

R$_1$ represents a hydrogen atom, a (C$_1$–C$_6$)alkyl, a (C$_3$–C$_6$) cycloalkyl, a group —CH$_2$CH$_2$COOH or a group —NR$_2$R$_3$;

R$_2$ and R$_3$ each represent, independently, a hydrogen atom or a (C$_1$–C$_6$)alkyl.

DETAILED DESCRIPTION OF THE INVENTION

The compounds of formula (I) comprise three asymmetric carbon atoms; the carbon atom bearing the substituent —CON(CH$_3$)$_2$ has the (S) configuration, the carbon atom bearing the substituent —OCOR$_1$ has the (R) configuration, and the carbon atom at position 3 of the indol-2-one has the (R) configuration.

The compounds of the formula (I) can exist in the form of bases or of addition salts with organic or inorganic bases, such as the salts with alkali metals or alkaline-earth metals, or the salts with organic or inorganic amines. Such addition salts are part of the invention.

These salts are advantageously prepared with pharmaceutically acceptable bases, but the salts of other bases which are of use, for example for purifying or isolating the compounds of the formula (I), are also part of the invention.

The compounds of formula (I) can exist in the form of hydrates or solvates, namely in the form of associations or combinations with one or more water molecules or with a solvent. Such hydrates and solvates are also part of the invention.

The term "alkyl" is intended to mean a linear or branched alkyl radical of one to six carbon atoms, such as the methyl, ethyl, propyl, isopropyl, butyl, isobutyl, tert-butyl, pentyl, isopentyl, hexyl or isohexyl radical.

The term "cycloalkyl" is intended to mean a cyclic alkyl radical of three to six carbon atoms, such as the cyclopropyl, cyclobutyl, cyclopentyl or cyclohexyl radical.

Among the compounds of formula (I), which are subjects of the invention, mention may be made of the preferred compounds, which are defined as follows:

R$_1$ represents a hydrogen atom, a methyl radical, an ethyl radical, an isopropyl radical, a cyclohexyl radical, a group —CH$_2$CH$_2$COOH, an amino group or a dimethylamino group;

in the form of a base or of an addition salt with an organic or inorganic base, and also in the hydrate or solvate form.

Among the compounds of formula (I) which are subjects of the invention, mention may in particular be made of the following compounds:

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl acetate;

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl propionate;

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl formate;

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl cyclohexanecarboxylate;

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl 2-methyl propanoate;

4-[[(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl]oxy]-4-oxobutanoic acid;

(2S,4R)-4-[(aminocarbonyl)oxy]-1-[(3R)-5-chloro-1-[(2,4-dimethoxyphenyl)sulfonyl]-3-(2-methoxyphenyl)-2-oxo-2,3-dihydro-1H-indol-3-yl]-N,N-dimethyl-2-pyrrolidinecarboxamide;

(2S,4R)-4-[[(dimethylamino)carbonyl]oxy]-1-[(3R)-5-chloro-1-[(2,4-dimethoxyphenyl)sulfonyl]-3-(2-methoxyphenyl)-2-oxo-2,3-dihydro-1H-indol-3-yl]-N,N-dimethyl-2-pyrrolidinecarboxamide;

The compounds mentioned hereinabove may be in the form of a base or of an addition salt with an organic or inorganic base, and also in the hydrate or solvate form.

According to another of its aspects, a subject of the present invention is a method for preparing the compounds of formula (I) characterized in that:

(2S,4R)-1-[5-chloro-1-[(2,4-dimethoxyphenyl)sulfonyl]-3-(2-methoxyphenyl)-2-oxo-2,3-dihydro-1H-indol-3-yl]-4-hydroxy-N,N-dimethyl-2-pyrrolidinecarboxamide, the levorotatory isomer, of formula:

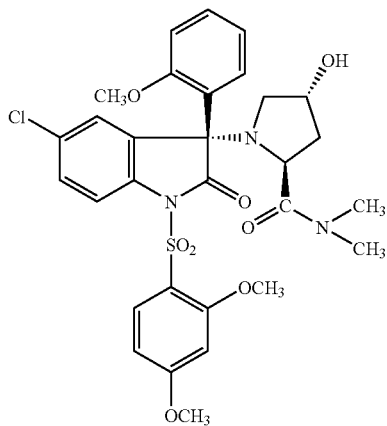

(compound A)

is reacted with a functional derivative of an acid of formula:

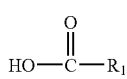

(II)

in which $R_1$ is as defined for a compound of formula (I).

Optionally, the compound of formula (I) is converted into one of its addition salts with a base.

As functional derivative of the acid of formula (II), use may be made of the acid chloride, an anhydride or the free acid itself.

When an acid chloride is used, the reaction is carried out in a solvent such as a chlorinated solvent, such as dichloromethane, dichloroethane or chloroform, an ether such as tetrahydrofuran, dioxane, or an amide such as N,N-dimethylformamide, in the presence of a base such as triethylamine, N-methylmorpholine, pyridine, 4-dimethylaminopyridine or N,N-diisopropylethylamine, and at a temperature of between −60° C. and ambient temperature.

When an anhydride is used, the reaction is carried out in the presence or absence of a base such as pyridine or 4-(dimethylamino)pyridine, in a solvent or in the absence of solvent, at a temperature between ambient temperature and the reflux temperature of the reaction medium. When a solvent is used, said solvent can be chosen from a chlorinated solvent such as dichloromethane, and an aromatic solvent such as toluene.

A compound of formula (I) in which $R_1$ represents a group —$CH_2CH_2COOH$ can also be prepared by reacting the compound A with succinic anhydride, in the presence of a base such as pyridine, in a solvent or in the absence of solvent, and at a temperature of between ambient temperature and the reflux temperature of the reaction medium.

When the acid itself is used, the reaction is carried out using a condensing agent such as a carbodiimide, for instance 1,3-dicyclohexylcarbodiimide or 1,3-diisopropylcarbodiimide, or an imidazole, for instance 1,1'-oxalyldiimidazol or N,N'-carbonyldiimidazole. The reaction is carried out in the presence or absence of a base such as triethylamine, N,N-diisopropylethylamine, pyridine, 4-dimethylaminopyridine or N-methylmorpholine, in a solvent such as a chlorinated solvent, for instance dichloromethane, dichloroethane or chloroform, an ester, for instance ethyl acetate, an ether, for instance diethyl ether, diisopropylether, tetrahydrofuran or dioxane, a nitrile, for instance acetonitrile, an amide, for instance N,N-dimethylformamide, or an aromatic hydrocarbon solvent, for instance toluene or xylene, and at a temperature range of from about −20° C. to about 80° C.

When the acid itself is used, the reaction can also be carried out in the presence of an acid catalyst such as an inorganic acid, for instance hydrochloric acid, hydrobromic acid or sulfuric acid, an organic acid, for instance acetic acid, formic acid, oxalic acid, or p-toluenesulfonic acid, or a Lewis acid, for instance boron trichloride, boron trifluoride or boron tribromide. The reaction is carried out in a solvent such as a chlorinated solvent, for instance dichloromethane, dichloroethane or chloroform, an ether, for instance diethyl ether, diisopropyl ether, tetrahydrofuran or dioxane, a ketone, for instance acetone, methylethyl acetone or methylisobutyl ketone, a nitrile, for instance acetonitrile, or an amide, for instance N,N-dimethylformamide, and at a temperature range of from about 0° C. and the reflux temperature of the solvent.

A compound of formula (I) in which $R_1$ represents a hydrogen atom can also be prepared by reacting the compound A with formic acid, in the presence of acetic anhydride and of a base such as pyridine, at a temperature of between 0° C. and ambient temperature.

According to a variant of the method and when $R_1$ represents a group —$NR_2R_3$:

a) the compound A is reacted, in the presence of a base, with phenyl chloroformate so as to obtain the compound B of formula:

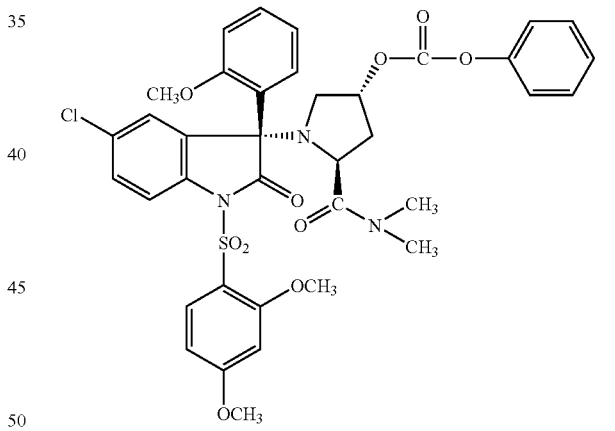

(compound B)

b) the compound B is reacted with a compound of formula:

 (III)

in which $R_2$ and $R_3$ are as defined hereinabove for a compound of formula (I), so as to obtain a compound of formula (I) in which $R_1$=$NR_2R_3$.

In step a), the compound A is reacted with phenyl chloroformate in the presence of a base such as pyridine or triethylamine, in a solvent such as dichloromethane or without solvent, and at a temperature range of from about 0° C. and about 100° C.

In step b), the reaction of the compound B with the compound of the formula (III) is carried out in a solvent such as dichloromethane or tetrahydrofuran or a mixture of these solvents, and at a temperature range of from about −60° C. and the reflux temperature of the solvent.

The compounds of formula (I) thus obtained can be subsequently separated from the reaction medium and purified according to conventional methods, for example by crystallization or chromatography.

The compound A is prepared according to the method described in application WO 01/55130; which is incorporated herein by reference in its entirety.

The functional derivatives of the acids of the formula (II) are commercially available, known, or prepared according to known methods.

According to another of its aspects, a subject of the invention is also the compound B. This compound is of use as a synthetic intermediate for the compounds of formula (I) in which $R_1=NR_2R_3$.

The following EXAMPLES describe the preparation of some compounds in accordance with the invention. These examples are not limiting and merely illustrate the present invention. The numbers of the compounds given in example refer to those given in the table below, which illustrates the chemical structures and the physical properties of some compounds according to the invention.

In the examples, the following abbreviations are used:
EtOAc: ethyl acetate
ether: diethyl ether
iso ether: diisopropyl ether
DCM: dichloromethane
M.p.: melting point
AT: ambient temperature
B.p.: boiling point
HPLC: high performance liquid chromatography.

The proton magnetic resonance spectra ($^1$H NMR) are recorded at 200 MHz in $d_6$-DMSO using the $d_6$-DMSO peak as reference. The chemical shifts δ are expressed as parts per million (ppm). The signals observed are expressed thus: s: singlet; bs: broad singlet; d: doublet; dd: doublet of doublets; t: triplet; q: quartet; up: unresolved peak; mt: multiplet.

The NMR spectra confirm the structures of the compounds.

EXAMPLE 1

Compound No. 1

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl acetate.

(I): $R_1$=—$CH_3$.

A mixture of 30 g of (2S,4R)-1-[5-chloro-1-[(2,4-dimethoxyphenyl)sulfonyl]-3-(2-methoxyphenyl)-2-oxo-2,3-dihydro-1H-indol-3-yl]-4-hydroxy-N,N-dimethyl-2-pyrrolidinecarboxamide, the levorotatory isomer (compound A), 1.45 g of 4-(dimethylamino)pyridine and 300 ml of acetic anhydride is refluxed for two hours and 30 minutes. After cooling the reaction mixture to ambient temperature, 170 ml of absolute ethanol are added. The mixture is concentrated under vacuum, the residue is extracted with 1000 ml of EtOAc, the organic phase is washed with 670 ml of a saturated aqueous $NH_4Cl$ solution and twice with an aqueous $NaHCO_3$ solution, and the solvent is evaporated off under vacuum. The residue is taken up in 190 ml of 2-propanol, and the mixture is refluxed then cooled to ambient temperature. The mixture is concentrated under vacuum, and the residue is taken up in iso ether and left to crystallize. The crystallized product formed is spin-filtered off, washed with iso ether and dried to obtain 30.28 g of the expected product, M.p.=194–195° C.

$\alpha^{25}_D$=−133.9° (c=0.5; acetonitrile). $^1$H NMR: $d_6$-DMSO: δ (ppm): 1.7 to 2.8: up: 13H; 3.3: bs: 3H, 3.7: s: 3H, 3.9: s: 3H, 4.6: mt: 1H, 5.2: mt: 1H, 6.6 to 8.2: up: 10H.

EXAMPLE 2

Compound No. 2

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl propionate.

(I): $R_1$=—$CH_2CH_3$.

A mixture of 5 g of the compound A, 0.24 ml of 4-(dimethylamino)pyridine and 50 ml of propionic anhydride is refluxed for two hours and 30 minutes. After cooling the reaction mixture to AT, 28 ml of absolute ethanol are added. The mixture is concentrated under vacuum, the residue is extracted with 60 ml of EtOAc, the organic phase is washed with 100 ml of a saturated aqueous NaCl solution and three times with 110 ml of a 10% aqueous $NaHCO_3$ solution, and the solvent is evaporated off under vacuum. The residue is taken up in iso ether and the precipitate formed is spin-filtered off to obtain 4.31 g of the expected product.

$\alpha^{25}_D$=−107° (c=0.5; acetonitrile). $^1$H NMR: $d_6$-DMSO: δ (ppm): 0.95: t: 2H, 1.6 to 2.7: up: 12H, 3.3: bs: 3H, 3.6: s: 3H, 3.8: s: 3H, 4.5: mt: 1H, 5.15 mt: 1H, 6.6 to 8.2: up: 11H.

EXAMPLE 3

Compound No. 3

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl formate.

(I): $R_1$=H.

4 ml of formic acid are cooled to 0° C., 1.6 ml of acetic anhydride are added dropwise, and the mixture is left for 4 hours with stirring at a temperature of less than 20° C. The reaction mixture is cooled in a bath of ice, a solution of 0.63 g of the compound A in 7 ml of pyridine is added, in 5 minutes, the mixture is dried beforehand, cooled in a bath of ice and left for 48 hours with stirring at AT. Water is added to the reaction mixture, which is extracted with EtOAc, the organic phase is washed with water and with a saturated NaCl solution and dried over $Na_2SO_4$, and the solvent is evaporated off under vacuum. The residue is chromatographed on silica gel, eluting with a DCM/EtOAc mixture (70/30; v/v). 0.27 g of the expected product is obtained. After solidification in a DCM/iso ether mixture (80/20; v/v), the expected product is obtained in the form of a powder containing 0.5 mol of iso ether, M.p.=127° C.

$\alpha^{25}_D$=−173° (c=0.11; chloroform).

EXAMPLE 4

Compound No. 4

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl cyclohexanecarboxylate.

(I):

$R_1 =$ 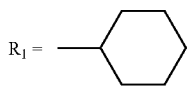

A mixture of 1.5 g of the compound A, 0.630 ml of cyclohexanecarbonyl chloride, 0.62 g of N,N-diisopropylethylamine and a few crystals of 4-(dimethylamino)pyridine in 20 ml of DCM is left to stir for 8 days at AT. The mixture is concentrated under vacuum, the residue is taken up in an EtOAc/water mixture, the mixture is basified by adding solid NaHCO$_3$, and separated by settling out, the organic phase is washed twice with a saturated. K$_2$CO$_3$ solution and with a saturated NaCl solution, and dried over Na$_2$SO$_4$, and the solvent is evaporated off under vacuum. The residue is chromatographed on silica gel, eluting with an EtOAc/DCM mixture (80/20; v/v). The product obtained is taken up in 5 ml of iso ether and left to stir for 48 hours at AT, the precipitate formed is spin-filtered and 1.0 g of the expected product is obtained, M.p.=197–198° C. The spin-filtration liquor is concentrated under vacuum and the solid obtained is crystallized from a DCM/iso ether mixture. A further 0.9 g of the expected product is obtained in the form of crystals, M.p.=197–200° C.

$\alpha^{25}_D = -144°$ (c=0.18; chloroform).

EXAMPLE 5

Compound No. 5

(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl 2-methyl propanoate.

(I): $R_1$=—CH(CH$_3$)$_2$

A mixture of 1.5 g of the compound A, 0.75 ml of isobutyryl chloride and 1.22 g of N,N-diisopropylethylamine in 20 ml of DCM is left to stir for 36 hours at AT. The mixture is concentrated under vacuum, the residue is taken up with water, basified by adding solid NaHCO$_3$, and extracted with EtOAc, the organic phase is washed with water and dried over Na$_2$SO$_4$, and the solvent is evaporated off under vacuum. The residue is chromatographed on silica gel, eluting with a DCM/EtOAc mixture (70/30; v/v) to obtain 1.17 g of the expected product after solidification in an EtOAc/iso ether mixture, M.p.=183–185° C.

$\alpha^{25}_D = -172°$ (c=0.15; chloroform).

EXAMPLE 6

Compound No. 6

4-[[(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl]oxy]-4-oxobutanoic acid.

(I): $R_1$=—CH$_2$CH$_2$COOH.

A mixture of 0.2 g of the compound A, 0.2 g of succinic anhydride and 3 ml of pyridine is heated at 50° C. for 5 minutes, until dissolution, and left to stir for 20 hours at 25° C. The mixture is concentrated under vacuum, the residue is taken up with a 2N HCl solution, extracted with ether and separated by settling out, and the precipitate formed in the organic phase is spin-filtered and washed with ether to obtain 0.2 g of the expected product in the form of crystals, M.p.=225–228° C.

$\alpha^{25}_D = -252°$ (c=0.25; chloroform). $^1$H NMR: d$_6$-DMSO: δ (ppm): 1.6 to 1.9: up: 2H; 2.2 to 2.6: up: 12H, 3.0 to 3.4: bs: 3H, 3.5 to 3.7: bs: 3H, 3.7 to 3.9: bs: 3H, 4.4 to 4.6: up: 1H, 5.1 to 5.3: up: 1H, 6.6 to 7.0: up: 5H, 7.26: t: 1H, 7.39: dd: 1H, 7.6 to 7.8: up: 2H, 7.94: d: 1H, 12.0: bs: 1H.

EXAMPLE 7

Compound No. 7

(2S,4R)-4-[(aminocarbonyl)oxy]-1-[(3R)-5-chloro-1-[(2,4-dimethoxyphenyl)sulfonyl]-3-(2-methoxyphenyl)-2-oxo-2,3-dihydro-1H-indol-3-yl]-N,N-dimethyl-2-pyrrolidinecarboxamide.

(I): $R_1$=—NH$_2$.

(A) (2S,4R)-4-[(phenoxycarbonyl)oxy]-1-[(3R)-5-chloro-1-[(2,4-dimethoxyphenyl)sulfonyl]-3-(2-methoxyphenyl)-2-oxo-2,3-dihydro-1H-indol-3-yl]-N,N-dimethyl-2-pyrrolidinecarboxamide.

4 ml of phenyl chloroformate are added, at 25° C., to a solution of 1.6 g of compound A in 20 ml of pyridine, and the mixture is left to stir for 20 hours at 25° C. The reaction mixture is concentrated under vacuum, the residue is taken up with a 1N HCl solution and extracted with EtOAc, the organic phase is dried over Na$_2$SO$_4$, and the solvent is evaporated off under vacuum to obtain 1.23 g of the expected product after titration in iso ether, M.p.=115–125° C.

(B) (2S,4R)-4-[(aminocarbonyl)oxy]-1-[(3R)-5-chloro-1-[(2,4-dimethoxyphenyl)sulfonyl]-3-(2-methoxyphenyl)-2-oxo-2,3-dihydro-1H-indol-3-yl]-N,N-dimethyl-2-pyrrolidinecarboxamide.

A solution of 0.7 g of the compound obtained in the preceding step, in 15 ml of THF, is cooled to −60° C., 4 g of NH$_3$ gas are added by sparging, and the mixture is left to stir for 5 hours, allowing the temperature to return to, and keeping it at, 0° C. The reaction mixture is concentrated under vacuum and the residue is chromatographed on silica gel, eluting with DCM and then EtOAc to obtain 0.37 g of the expected product after titration in iso ether, M.p.=155–165° C.

$\alpha^{25}_D = -184°$ (c=0.25; chloroform).

EXAMPLE 8

Compound No. 8

(2S,4R)-4-[[(dimethylamino)carbonyl]oxy]-1-[(3R)-5-chloro-1-[(2,4-dimethoxyphenyl)sulfonyl]-3-(2-methoxyphenyl)-2-oxo-2,3-dihydro-1H-indol-3-yl]-N,N-dimethyl-2-pyrrolidinecarboxamide.

(I): $R_1$=—N(CH$_3$)$_2$.

A mixture of 0.35 g of the compound obtained in step A of Example 7 and 10 ml of a 2M solution of dimethylamine in THF is left to stir for 20 hours at 25° C. The reaction mixture is concentrated under vacuum, the residue is triturated in iso ether under hot conditions, and the precipitate formed is spin-filtered to obtain 0.18 g of the expected product, M.p.=138–140° C.

$\alpha^{25}{}_D = -152°$ (c=0.25; chloroform).

Table I below summarizes the chemical structures and the physical properties of a few of the examples of compounds according to the invention.

TABLE I

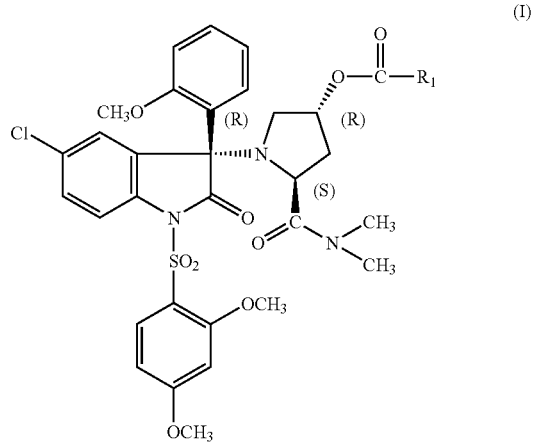

(I)

| Compounds Nos. | $R_1$ | M.p. ° C. Crystallization solvent $\alpha^{25}{}_d$ = (chloroform) |
|---|---|---|
| 1 | —CH$_3$ | 194–195<br>iso ether<br>−133.9° (c = 0.5; acetonitrile) |
| 2 | —CH$_2$CH$_3$ | —<br>iso ether<br>−107° (c = 0.5; acetonitrile) |
| 3 | H | 127<br>DCM/iso ether<br>−173° (c = 0.11) |
| 4 | —⟨cyclohexyl⟩ | 197–200<br>DCM/iso ether<br>−144° (c = 0.18) |
| 5 | —CH(CH$_3$)$_2$ | 183–185<br>EtOAc/iso ether<br>−172° (c = 0.15) |
| 6 | —CH$_2$CH$_2$COOH | 225–228<br>ether<br>−252° (c = 0.25) |
| 7 | —NH$_2$ | 155–165<br>iso ether<br>−184° (c = 0.25) |
| 8 | N(CH$_3$)$_2$ | 138–140<br>iso ether<br>−152° (c = 0.25) |

The compounds according to the invention were the subject of biochemical studies.

The affinity of the compounds of formula (I) according to the invention, for $V_{1b}$ receptors for arginine-vasopressin, was determined in vitro using the method described by Y. DE KEYSER et al., Febs Letters, 1994, 356, 215–220. This method consists in studying, in vitro, the displacement of triturated arginine-vasopressin ([$^3$H]-AVP) to $V_{1b}$ receptors present on cellular or adenohypophyseal membrane preparations bearing rat or human $V_{1b}$ receptors. The 50% inhibitory concentrations (IC$_{50}$) for the binding of the triturated arginine-vasopressin, of the compounds according to the invention, are generally less than $5.0 \times 10^{-9}$M. For example, the compound of Example 1 has an IC$_{50}$ of $3.4 \times 10^{-9}$M for human $V_{1b}$ receptors.

The affinity of the compounds of formula (I) according to the invention, for $V_{1a}$ receptors for arginine-vasopressin, was determined in vitro using the method described by M. THIBONNIER et al., J. Biol. Chem., 1994, 269, 3304–3310. This method consists in studying, in vitro, the displacement of triturated arginine-vasopressin ([$^3$H]-AVP) to $V_{1a}$ receptors present on cellular or membrane preparations bearing rat or human $V_{1a}$ receptors. Some compounds of formula (I) also exhibit an affinity for $V_{1a}$ receptors for arginine-vasopressin, with IC$_{50}$ values of the order of $10^{-8}$M. For example, the compound of Example 1 has an IC$_{50}$ of $8.4 \times 10^{-8}$M for human $V_{1a}$ receptors.

The compound A of the prior art has an IC$_{50}$ of $1.0 \times 10^{-8}$M for human $V_{1b}$ receptors and an IC$_{50}$ of $3.1 \times 10^{-7}$M for human $V_{1a}$ receptors.

The affinity of the compounds of formula (I) according to the invention, for $V_2$ receptors of vasopressin, was also studied (method described by M. Birnbaumer et al., Nature (Lond.), 1992, 357, 333–335). The compounds studied have little or no affinity for $V_2$ receptors.

The compounds according to the invention can therefore be used for preparing medicinal products, in particular medicinal products intended to prevent or treat any pathological condition in which arginine-vasopressin and/or its $V_{1b}$ receptors, or both its $V_{1b}$ receptors and its $V_{1a}$ receptors, are involved.

Thus, according to another of its aspects, a subject of the invention is medicinal products which comprise a compound of formula (I), or an addition salt of the latter with a pharmaceutically acceptable base, or else a solvent or a hydrate of the compound of formula (I).

Thus, the compounds according to the invention can be used, in humans or in animals, in the treatment or prevention of various vasopressin-dependent conditions, such as cardiovascular conditions, for example hypertension, pulmonary hypertension, cardiac insufficiency, myocardial infarction or coronary vasospasm, in particular in smokers, Raynaud's disease, and unstable angina and PTCA (percutaneous transluminal coronary angioplasty), cardiac ischaemia or disturbances of haemostasis; conditions of the central nervous system, such as migraine, cerebral vasospasm, cerebral hemorrhage, cerebral edema, depression, anxiety, stress, emotional disorders, obsessive-compulsive disorder, panic attacks, psychotic states or memory disorders, for example; conditions of the renal system, such as renal vasospasm, necrosis of the renal cortex or nephrogenic diabetes insipidus; conditions of the gastric system, such as gastric vasospasm, cirrhosis of the liver, ulcers or the pathology of vomiting, for example nausea, including nausea due to chemotherapy or travel sickness; or diabetic nephropathy. The compounds according to the invention can also be used in the treatment of disorders of sexual behavior; in women, the compounds according to the invention can be used to treat dysmenorrhea or premature labor. The compounds according to the invention can also be used in the treatment of small cell lung cancers; hyponatremic encephalopathy; pulmonary syndromes; Menière's disease; glaucoma, cataracts; obesity; type II diabetes; atherosclerosis; Cushing's syndrome; insulin resistance; or hypertriglyceridaemia; or in post-operative treatments, in particular after abdominal surgery.

The compounds according to the invention can also be used in the treatment or prevention of any pathological conditions resulting from stress, such as fatigue and its syndromes, ACTH-dependent disorders, cardiac disorders, pain, modifications in gastric emptying, in fecal excretion (colitis, irritable bowel syndrome or Crohn's disease) or in acid secretion, hyperglycemia, immunosuppression, inflammatory processes (rheumatoid arthritis and osteoarthritis), multiple infections, cancers, asthma, psoriasis, allergies and various neuropsychiatric disorders, such as anorexia nervosa, bulimia, mood disorders, depression, anxiety, sleep disorders, states of panic, phobias, obsession, disorders of pain perception (fibromyalgia), neurodegenerative diseases (Alzheimer's disease, Parkinson's disease or Huntingdon's disease), drug addiction, hemorrhagic stress, muscle spasms or hypoglycemia. The compounds according to the invention can also be used in the treatment or prevention of chronic stress conditions, such as immunodepression, fertility problems or dysfunctioning of the hypothalamo-pituitary-adrenal axis.

The compounds according to the invention can also be used as psychostimulants, resulting in an increase in alertness or emotional reactivity to the surroundings, and making adaptation easier.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, a solvate or a hydrate of said compound, and also at least one pharmaceutically acceptable excipient.

Said excipients are chosen, depending on the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its possible salt, solvate or hydrate, can be administered in a single-dose administration form, as a mixture with conventional pharmaceutical excipients, to animals and to humans, for the prophylaxis for or treatment of the disorders or diseases mentioned hereinabove.

The suitable single-dose administration forms comprise forms for oral administration, such as tablets, soft or hard gelatin capsules, powders, granules and oral solutions or suspensions, forms for sublingual, buccal, intratracheal, intraocular or intranasal administration, forms for administration by inhalation, forms for topical, transdermal, subcutaneous, intramuscular or intravenous administration, forms for rectal administration and implants. For topical application, the compounds according to the invention can be used in creams, gels, ointments or lotions.

By way of example, a single-dose administration form of a compound according to the invention, in tablet form, can comprise the following components:

| Compound according to the invention | 50.0 mg |
|---|---|
| Mannitol | 223.75 mg |
| Sodium croscaramellose | 6.0 mg |
| Cornstarch | 15.0 mg |
| Hydroxypropylmethylcellulose | 2.25 mg |
| Magnesium stearate | 3.0 mg |

By oral administration, the dose of active principle administered per day can reach 0.01 to 100 mg/kg, taken in one or more doses, preferentially 0.02 to 50 mg/kg.

There may be particular cases where higher or lower doses are appropriate; such doses do not depart from the context of the invention. According to usual practice, the dose suitable for each patient is determined by the physician according to the method of administration, and the weight and response of said patient.

According to another of its aspects, the present invention also relates to a method of treating the pathological conditions indicated above, which comprises administering an effective dose of a compound according to the invention, or one of its pharmaceutically acceptable salts or hydrates or solvates, to a patient.

What is claimed is:
1. A compound corresponding to formula (I):

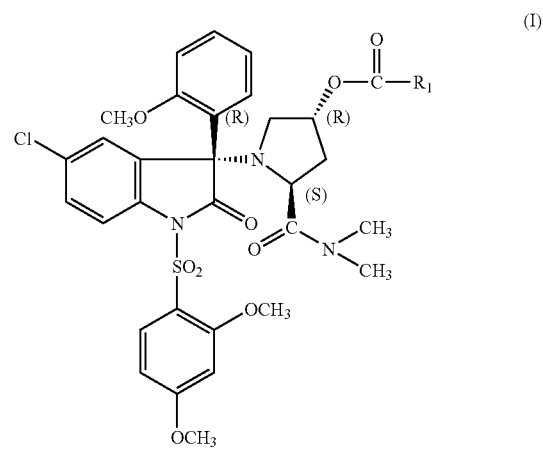

wherein:
R$_1$ is hydrogen, (C$_1$–C$_6$)alkyl, (C$_3$–C$_6$)cycloalkyl, —CH$_2$CH$_2$COOH or —NR$_2$R$_3$;
wherein
R$_2$ and R$_3$ each represent, independently, hydrogen or (C$_1$–C$_6$)alkyl; and said compound of formula (I) in the form of a base or of an addition salt with an organic or inorganic base, or a hydrate or a solvate thereof.

2. The compound of formula (I) as set forth in claim 1, wherein R$_1$ is hydrogen, methyl, ethyl, isopropyl, cyclohexyl, —CH$_2$CH$_2$COOH, amino or dimethylamino; and
in the form of a base or of an addition salt with an organic or inorganic base, or a hydrate or a solvate thereof.

3. A compound selected from the group consisting of:
(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl acetate;
(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl propionate;
(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl formate;
(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl cyclohexanecarboxylate;
(3R,5S)-1-[(3R)-5-chloro-1-[(2,4-dimethoxyphenyl)sulfonyl]-3-(2-methoxyphenyl)-2-oxo-2,3-dihydro-1H-indol-3-yl]-5-[(dimethylamino)carbonyl]-3-pyrrolidinyl 2-methyl propanoate;

4-[[(3R,5S)-1-[(3R)-5-chloro-1-[(2,4-dimethoxyphenyl) sulfonyl]-3-(2-methoxyphenyl)-2,3-dihydro-1H-indol-3-yl]-5-[(dimethylamino)carbonyl]-3-pyrrolidinyl] oxy]-4-oxobutanoic acid;

(2S,4R)-4-[(aminocarbonyl)oxy]-1-[(3R)-5-chloro-1-[(2, 4-dimethoxyphenyl)sulfonyl]-3-(2-methoxyphenyl)-2-oxo-2,3-dihydro-1H-indol-3-yl]-N,N-dimethyl-2-pyrrolidinecarboxamide; and (2S,4R)-4-[[(dimethylamino)carbonyl]oxy]-1-[(3R)-5-chloro-1-[(2,4-dimethoxyphenyl)sulfonyl]-3-(2-methoxyphenyl)-2-oxo-2,3-dihydro-1H-indol-3-yl]-N,N-dimethyl-2-pyrrolidinecarboxamide; and said compound in the form of a base or of an addition salt with an organic or inorganic base, or a hydrate or a solvate thereof.

4. A method for preparing a compound of formula (I) as set forth in claim 1, comprising:

reacting (2S,4R)-1-[5-chloro-1-[(2,4-dimethoxyphenyl) sulfonyl]-3-(2-methoxyphenyl)-2-oxo-2,3-dihydro-1H-indol-3-yl]-4-hydroxy-N,N-dimethyl-2-pyrrolidinecarboxamide, the levorotatory isomer, of formula:

(compound A)

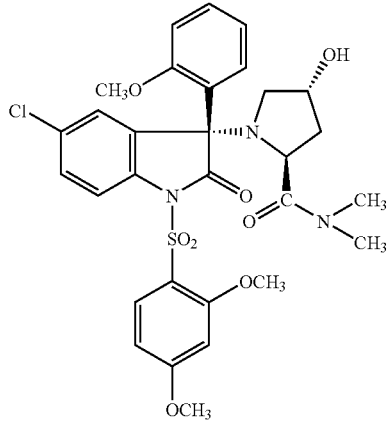

with a functional derivative of an acid of formula (II):

(II)

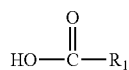

wherein $R_1$ is as defined for a compound of formula (I) in claim 1.

5. A method for preparing a compound of formula (I) as set forth in claim 1 in which $R_1$ is —$NR_2R_3$, comprising:

a) reacting compound A of formula:

(compound A)

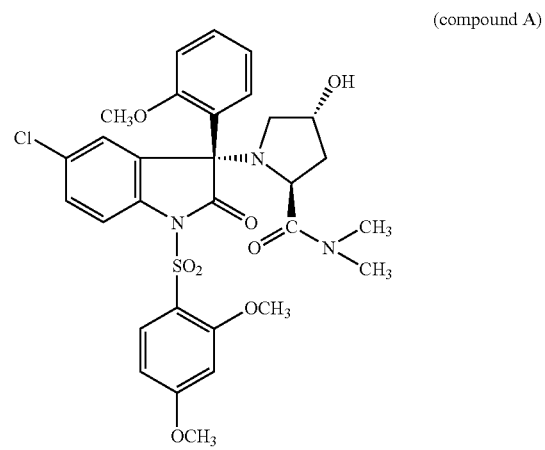

with phenyl chloroformate, in the presence of a base, so as to obtain compound B of formula:

(compound B)

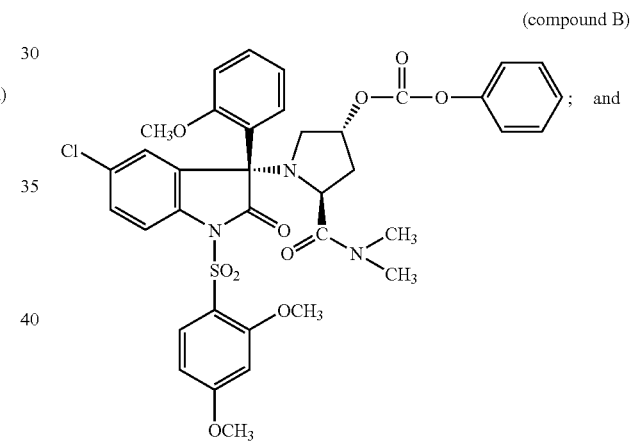

; and b) reacting the compound B with a compound of formula (III):

$HNR_2R_3$ (III)

wherein $R_2$ and $R_3$ are as defined for a compound of formula (I) in claim 1, so as to obtain a compound of formula (I) in which $R_1$=$NR_2R_3$.

6. A pharmaceutical composition comprising a compound of formula (I) as set forth in claim 1, or a pharmaceutically acceptable salt, a hydrate or a solvate thereof, in combination with at least one pharmaceutically acceptable excipient.

7. A pharmaceutical composition comprising one or more compounds as set forth in claim 3, or a pharmaceutically acceptable salt, a hydrate or a solvate thereof, in combination with at least one pharmaceutically acceptable excipient.

8. A method of treating a disease selected from the group consisting of stress, anxiety, depression, obsessive-compulsive disorder, panic attacks, atherosclerosis, dysmenorrhea and premature labor comprising administering to a patient suffering from said disease a therapeutically effective amount of a compound of formula (I) as set forth in claim 1.

9. A method of treating a disease selected from the group consisting or stress, anxiety, depression, obsessive-compulsive disorder and panic attacks comprising administering to a patient suffering from said disease a therapeutically effective amount of a compound as set forth in claim 3.

10. A method of treating atherosclerosis in a patient comprising administering to said patient a therapeutically effective amount of a compound as set forth in claim 3.

11. A method of treating dysmenorrhea or premature labor in a patient comprising administering to said patient a therapeutically effective amount of a compound as set forth in claim 3.

12. A method of treating stress comprising administering to a patient suffering from said disease a therapeutically effective amount of a compound as set forth in claim 3.

13. A method of treating anxiety comprising administering to a patient suffering from said disease a therapeutically effective amount of a compound as set forth in claim 3.

14. A method of treating depression comprising administering to a patient suffering from said disease a therapeutically effective amount of a compound as set forth in claim 3.

15. A. method of treating obsessive-compulsive disorder comprising administering to a patient suffering from said disease a therapeutically effective amount of a compound as set forth in claim 3.

16. A method of treating panic attacks comprising administering to a patient suffering from said disease a therapeutically effective amount of a compound as set forth in claim 3.

* * * * *